US011694781B1

(12) United States Patent
Cook et al.

(10) Patent No.: US 11,694,781 B1
(45) Date of Patent: Jul. 4, 2023

(54) SYSTEM AND METHOD FOR SUPPLY CHAIN OF PHARMACEUTICALS AND OTHER GOODS

(71) Applicant: WALGREEN CO., Deerfield, IL (US)

(72) Inventors: Matthew Cook, Long Grove, IL (US); Rex A. Swords, Cedar Hill, TX (US); Michael Bleser, Deerfield, IL (US); William Sunna, Wheeling, IL (US)

(73) Assignee: WALGREEN CO., Deerfield, IL (US)

( * ) Notice: Subject to any disclaimer, the term of this patent is extended or adjusted under 35 U.S.C. 154(b) by 332 days.

(21) Appl. No.: 17/063,645

(22) Filed: Oct. 5, 2020

(51) Int. Cl.
| | |
|---|---|
| *G16H 20/10* | (2018.01) |
| *G06Q 10/0832* | (2023.01) |
| *G06Q 10/087* | (2023.01) |
| *G16H 40/63* | (2018.01) |

(52) U.S. Cl.
CPC ........... *G16H 20/10* (2018.01); *G06Q 10/087* (2013.01); *G06Q 10/0832* (2013.01); *G16H 40/63* (2018.01)

(58) Field of Classification Search
CPC .... G16H 20/10; G16H 40/63; G06Q 10/0832; G06Q 10/087
See application file for complete search history.

(56) References Cited

U.S. PATENT DOCUMENTS

| 11,373,247 | B2 * | 6/2022 | Rutherford | ............ G16H 10/60 |
| 2007/0050209 | A1 * | 3/2007 | Yered | ..................... G06Q 30/04 |
| | | | | 705/2 |
| 2013/0096938 | A1 * | 4/2013 | Stueckemann | ........ G16H 40/60 |
| | | | | 705/2 |
| 2013/0173287 | A1 * | 7/2013 | Cashman | ............... H04N 7/141 |
| | | | | 705/2 |
| 2014/0052463 | A1 * | 2/2014 | Cashman | ........... G06Q 10/1095 |
| | | | | 705/2 |
| 2014/0330579 | A1 * | 11/2014 | Cashman | ........... G06Q 10/1095 |
| | | | | 705/2 |
| 2016/0042148 | A1 * | 2/2016 | Bradley | ................. G16H 70/40 |
| | | | | 705/3 |
| 2022/0374836 | A1 * | 11/2022 | Miyamoto | ......... G06Q 10/0837 |

* cited by examiner

*Primary Examiner* — Michael Collins
(74) *Attorney, Agent, or Firm* — Marshall, Gerstein & Borun LLP; Randall G. Rueth

(57) ABSTRACT

The following relates generally to facilitating delivery of prescription medication. In some embodiments, a pharmacy computer system: (i) receives a prescription, (ii) reviews the prescription, and (iii) sends the prescription to an intermediate cloud layer. The intermediate cloud layer may then determine a warehouse to send the prescription to based on at least one criteria. The at least one criteria may comprise at least one of: (i) a health insurance plan; (ii) whether the medication comprises a controlled substance; (iii) whether the medication must be refrigerated during shipping; (iv) a warehouse shipping address; or (v) a fulfillment cap of a warehouse.

16 Claims, 8 Drawing Sheets

SYSTEM AND METHOD FOR SUPPLY CHAIN OF PHARMACEUTICALS AND OTHER GOODS

BACKGROUND

In the modern world, timely, efficient delivery of prescription medication is critically important. However, most modern delivery systems are general delivery systems, and do not account for the particulars of prescription medication delivery, thus resulting in delays and inefficiencies.

The systems and methods disclosed herein provide solutions to this problem and others.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is a computer system for facilitating delivery of prescription medication. The system may include a pharmacy computer system comprising one or more processors configured to: (i) receive a prescription, (ii) review the prescription, and (iii) send the prescription to an intermediate cloud layer. The system may further include the intermediate cloud layer comprising one or more processors configured to: receive the reviewed prescription from the pharmacy computer system; determine, based on at least one criteria, a warehouse of a plurality of warehouses to send medication of the prescription to, wherein the at least one criteria comprises at least one of: (i) a health insurance plan; (ii) whether the medication comprises a controlled substance; (iii) whether the medication must be refrigerated during shipping; (iv) a warehouse shipping address; or (v) a fulfillment cap of a warehouse; and send an indication of the determined warehouse of the plurality of warehouses to a warehouse computer system.

In another aspect, there is a computer-implemented method for facilitating delivery of prescription medication. The method may include, with one or more processors of a pharmacy computer system: (i) receiving a prescription, (ii) reviewing the prescription, and (iii) sending the prescription to an intermediate cloud layer comprising one or more processors. The method may further include, with the one or more processors of the intermediate cloud layer: receiving the reviewed prescription from the pharmacy computer system; determining, based on at least one criteria, a warehouse of a plurality of warehouses to send medication of the prescription to, wherein the at least one criteria comprises at least one of: (i) a health insurance plan; (ii) whether the medication comprises a controlled substance; (iii) whether the medication must be refrigerated during shipping; (iv) a warehouse shipping address; and (v) a fulfillment cap of a warehouse; or sending an indication of the determined warehouse of the plurality of warehouses to a warehouse computer system.

In yet another aspect, there is a computer system for facilitating delivery of prescription medication. The computer system may include: an intermediate warehouse computer system of an intermediate warehouse, the intermediate warehouse computer system comprising one or more processors configured to: receive a prescription; determine if the prescription is eligible to be filled by a central warehouse system; if the prescription is not eligible to be filled by the central warehouse system, send instructions to fill the prescription at the intermediate warehouse; and if the prescription is eligible to be filled by the central warehouse system, route the prescription to a central warehouse. The computer system may further include a central warehouse computer system of a central warehouse, the central warehouse computer system comprising one or more processors configured to: pull the prescription from a database; determine if the central warehouse can fill the prescription; if the central warehouse can fill the prescription, send instructions to deliver medication of the prescription from the central warehouse to the intermediate warehouse; and if the central warehouse cannot fill the prescription, push the prescription back to the intermediate warehouse.

BRIEF DESCRIPTION OF THE DRAWINGS

FIG. 5B is a continuation of the flowchart in FIG. 5A.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

The following discussion teaches systems and methods for, inter alia, facilitating delivery of prescription medication.

Exemplary Infrastructure

Figure 1:
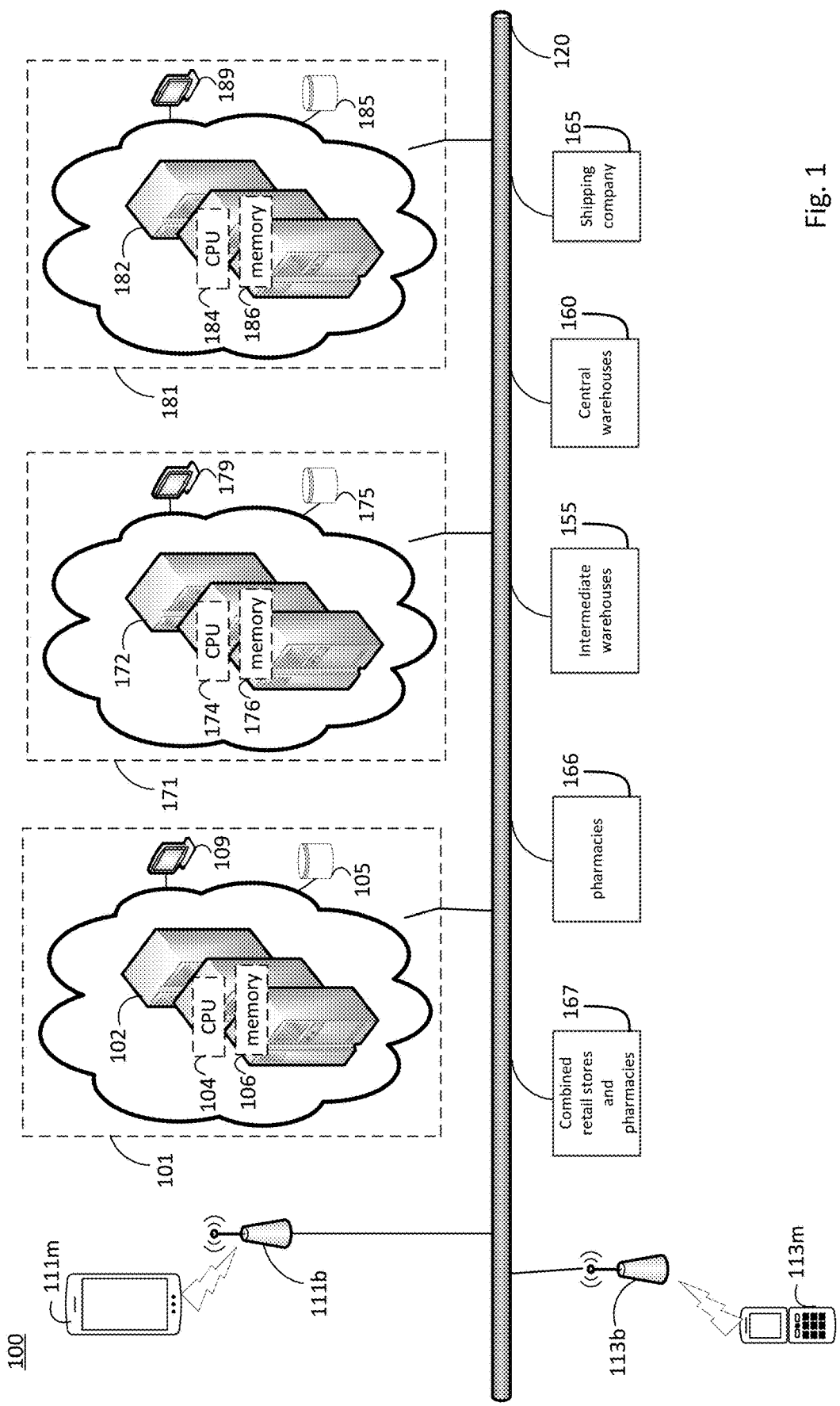
FIG. 1 illustrates a platform 100 configured for facilitating delivery of prescription medication in accordance with various embodiments disclosed herein.

FIG. 1 illustrates a platform 100 configured for facilitating delivery of prescription medication in accordance with various embodiments disclosed herein. In the example embodiment of FIG. 1, the platform 100 includes pharmacy computer system 101, intermediate cloud layer 171 (also referred to as pharmacy mail order hub 171), and warehouse computer system 181. In the example of FIG. 1, the pharmacy computer system 101 includes server(s) 102; intermediate cloud layer 171 includes server(s) 172; and the warehouse computer system 181 includes server(s) 182. In various embodiments, server(s) 102, 172, 182 comprise multiple servers, which may comprise multiple, redundant, or replicated servers as part of a server farm. In still further embodiments, server(s) 102, 172, 182 are implemented as cloud-based servers. For example, server(s) 102, 172, 182 may comprise a cloud-based platform such as MICROSOFT AZURE, AMAZON AWS, or the like.

As illustrated in the example of FIG. 1, server(s) 102, 172, 182 may include one or more processor(s) 104, 174, 184, respectively. As further illustrated, server(s) 102, 172, 182 may also include one or more computer memories 106, 176, 186, respectively. The memories 106, 176, 186 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 106, 176, 186 may store an operating system (OS) (e.g., Microsoft Windows, Linux, Unix, etc.) capable of facilitating the functionalities, apps, methods, or other software as discussed herein. The memories 106, 176, 186 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. It should be appreciated that one or more other applications may be envisioned and that are executed by the processor(s) 104, 174, 184.

The processor(s) 104, 174, 184 may be connected to the memories 106, 176, 186 via a computer bus responsible for transmitting electronic data, data packets, or otherwise electronic signals to and from the processor(s) 104, 174, 184 and memories 106, 176, 186 in order to implement or perform the machine readable instructions, methods, processes, elements or limitations, as illustrated, depicted, or described for the various flowcharts, illustrations, diagrams, figures, and/or other disclosure herein.

The processor(s) 104, 174, 184 may interface with the memory 106, 176, 186 via the computer bus to execute an operating system (OS). The processor(s) 104, 174, 184 may also interface with the memory 106, 176, 186 via the computer bus to create, read, update, delete, or otherwise access or interact with the data stored in the memories 106, 176, 186 and/or (as respectively shown in the example of FIG. 1) the databases 105, 171, 181 (e.g., a relational database, such as Oracle, DB2, MySQL, or a NoSQL based database, such as MongoDB). The data stored in the memories 106, 176, 186 and/or the databases 105, 175, 185 may include all or part of any of the data or information described herein, including, for example, prescription data, medication data, status data (e.g., delivery status data), patient data, identity data, and so forth.

The server(s) 102, 172, 182 may further include a communication component configured to communicate (e.g., send and receive) data via one or more external/network port(s) to one or more networks or local terminals, such as computer network 120 and/or terminals 109, 179, 189 (for rendering or visualizing) as illustrated in the example of FIG. 1, and as described herein. In some embodiments, server(s) 102, 172, 182 may include a client-server platform technology such as ASP.NET, Java J2EE, Ruby on Rails, Node.js, a web service or online API, responsive for receiving and responding to electronic requests. The server(s) 102, 172, 182 may implement the client-server platform technology that may interact, via the computer bus, with the memories(s) 106, 176, 186 (including the applications(s), component(s), API(s), data, etc. stored therein) and/or databases 105, 175, 185 to implement or perform the machine readable instructions, methods, processes, elements or limitations, as illustrated, depicted, or described for the various flowcharts, illustrations, diagrams, figures, and/or other disclosure herein. According to some embodiments, the server(s) 102, 172, 182 may include, or interact with, one or more transceivers (e.g., WWAN, WLAN, and/or WPAN transceivers) functioning in accordance with IEEE standards, 3GPP standards, 4G standards, 5G standards or other standards, and that may be used in receipt and transmission of data via external/network ports connected to computer network 120.

Server(s) 102, 172, 182 may further include or implement an operator interface configured to present information to an administrator or operator and/or receive inputs from the administrator or operator. As shown in FIG. 1, an operator interface may provide a display screen (e.g., via terminal 109, 179, 189). Server(s) 102, 172, 182 may also provide I/O components (e.g., ports, capacitive or resistive touch sensitive input panels, keys, buttons, lights, LEDs), which may be directly accessible via or attached to server(s) 102, 172, 182 or may be indirectly accessible via or attached to terminals 109, 179, 189. According to some embodiments, an administrator(s) or operator(s) may access the server(s) 102, 172, 182 via terminal 109, 179, 189 to review information, make changes, input training data, and/or perform other functions.

As described above herein, in some embodiments, server(s) 102, 172, 182 may perform the functionalities as discussed herein as part of a "cloud" network or may otherwise communicate with other hardware or software components within the cloud to send, retrieve, or otherwise analyze data or information described herein. Furthermore, server(s) 102, 172, 182 and/or their respective memorie(s) 106, 176, 186 are configured to store data including for example, patient data, pharmacy data, prescription data, and so forth.

In general, a computer program or computer based product, or application, in accordance with some embodiments may include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions may be installed on or otherwise adapted to be executed by the processor(s) 104, 174, 184 (e.g., working in connection with the respective operating system in memories 106, 176, 186) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, Actionscript, Javascript, HTML, CSS, XML, etc.).

In the example embodiment of FIG. 1, the pharmacy computer system 101, intermediate cloud layer 171, and warehouse computer system 181 are communicatively connected, via computer network 120 and base stations 111b and 113b to respective mobile devices 111m and 113m. Computer network 120 may comprise a packet based network operable to transmit computer data packets among the various devices and servers described herein. For example, computer network 120 may consist of any one or more of Ethernet based network, a private network, a local area network (LAN), and/or a wide area network (WAN), such as the Internet. In addition, in some embodiments, computer network 120 may comprise cellular or mobile networks to facilitate data packet traffic (e.g., mobile device movement data) to and from base stations 111*b* and/or 113*b*. Base stations 111*b* and 113*b* may comprise cellular towers or access points implementing any one or more cellular or mobile device standards, including, for example, any of GSM, UMTS, CDMA, NMT, LTE, 5G NR, or the like.

EXEMPLARY EMBODIMENTS

Figure 2:
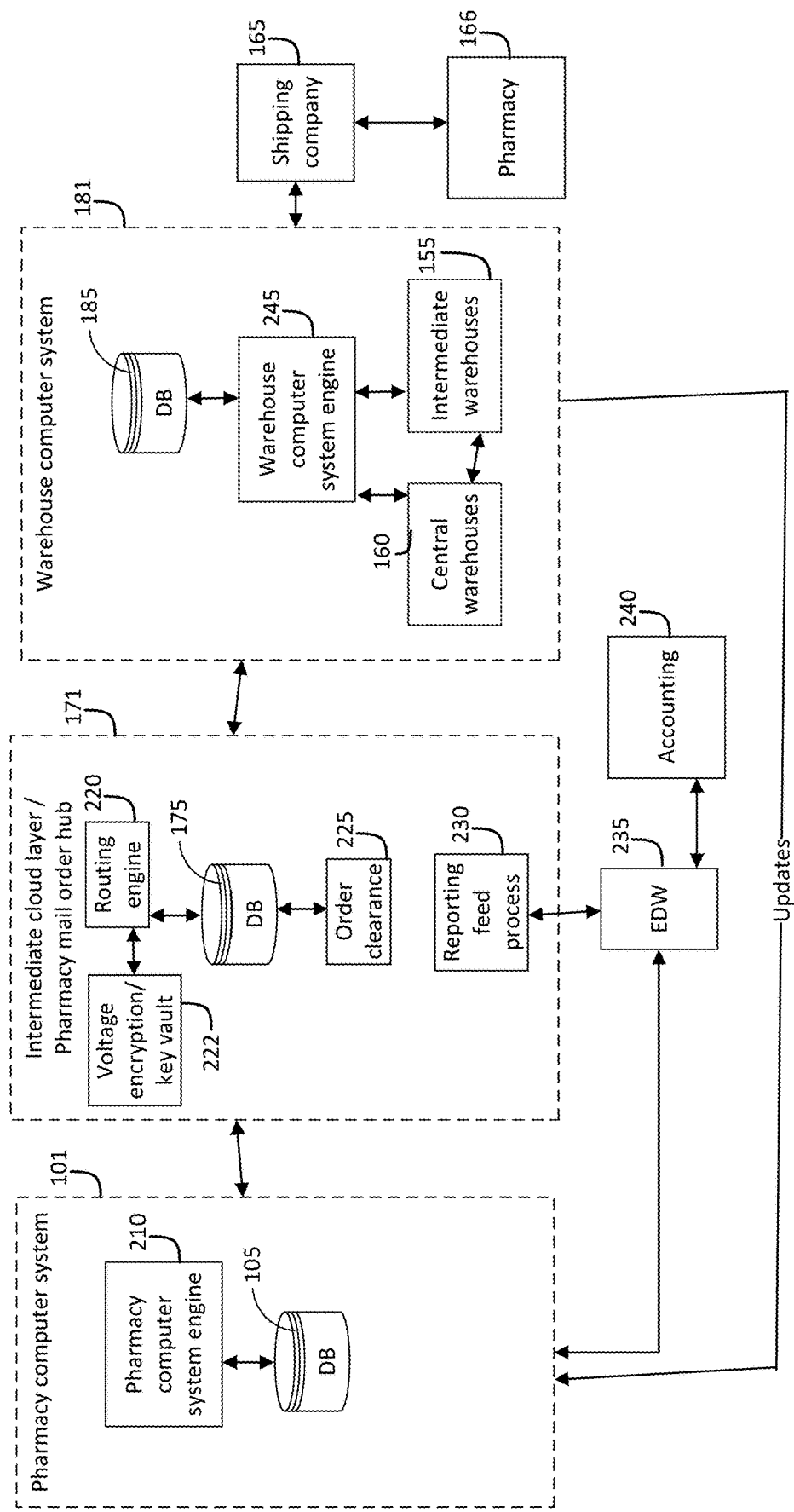
FIG. 2 shows an example system including a pharmacy computer system, an intermediate cloud layer, and warehouse computer system.

FIG. 2 shows an example system including a pharmacy computer system, an intermediate cloud layer, and warehouse computer system. In this regard, the example system of FIG. 2 may be configured to perform any of the example methods illustrated in any of FIGS. 3A-C.

Figure 3A:
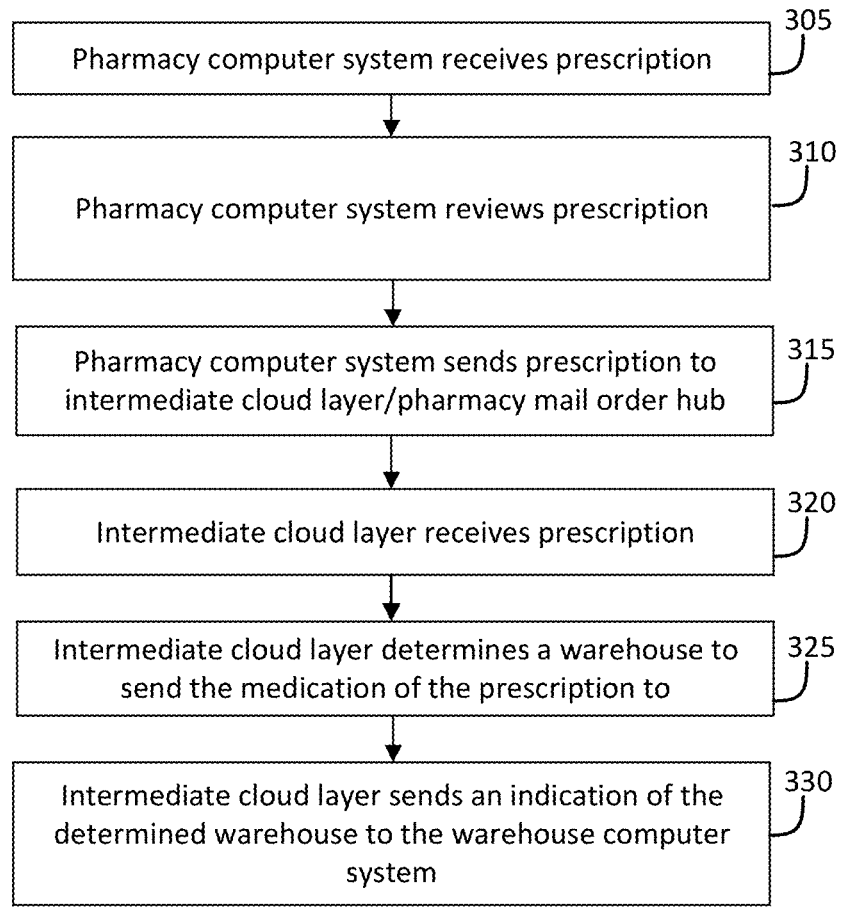
FIG. 3A shows an overview flowchart of an example process for facilitating delivery of prescription medication.

For instance, with reference to FIGS. 2 and 3A, at step 305, the pharmacy computer system 101 receives a prescription (e.g., from a mobile device 111*m* or 113*m*). At step 310, the pharmacy computer system 101 reviews the prescription. For example, the pharmacy computer system 101 may review the prescription by determining if a conflict exists between a medication of the prescription and another medication of a patient of the prescription. In another example, the pharmacy computer system 101 may review the prescription by determining an out of pocket payment for a patient of the prescription.

At step 315, the pharmacy computer system 101 sends the prescription to the intermediate cloud layer 171. Further, the prescription may be sent in a first file format, such as an order received (ODR) file. At step 320, the intermediate cloud layer 171 receives the prescription. At step 325, the intermediate cloud layer 171 determines a warehouse to send the medication of the prescription to. For example, the intermediate cloud layer 171 may determine the warehouse to send the medication of the prescription to based on any or all of the following criteria: (i) a health insurance plan of the patient; (ii) whether the medication comprises a controlled substance (e.g., controlled by state, local, or federal law); (iii) whether the medication must be refrigerated during shipping (e.g., should be part of a cold chain shipping process); (iv) a warehouse shipping address (e.g., the geographic location of the warehouse; in some embodiments, this criteria is instead a geographic proximity of the warehouse to the destination pharmacy); and (v) a fulfillment cap of a warehouse.

At step 330, intermediate cloud layer 101 sends an indication of the determined warehouse to the warehouse computer system 181. The indication may be sent in a second file format, such as an order completion (ODC) file.

Figure 3B:
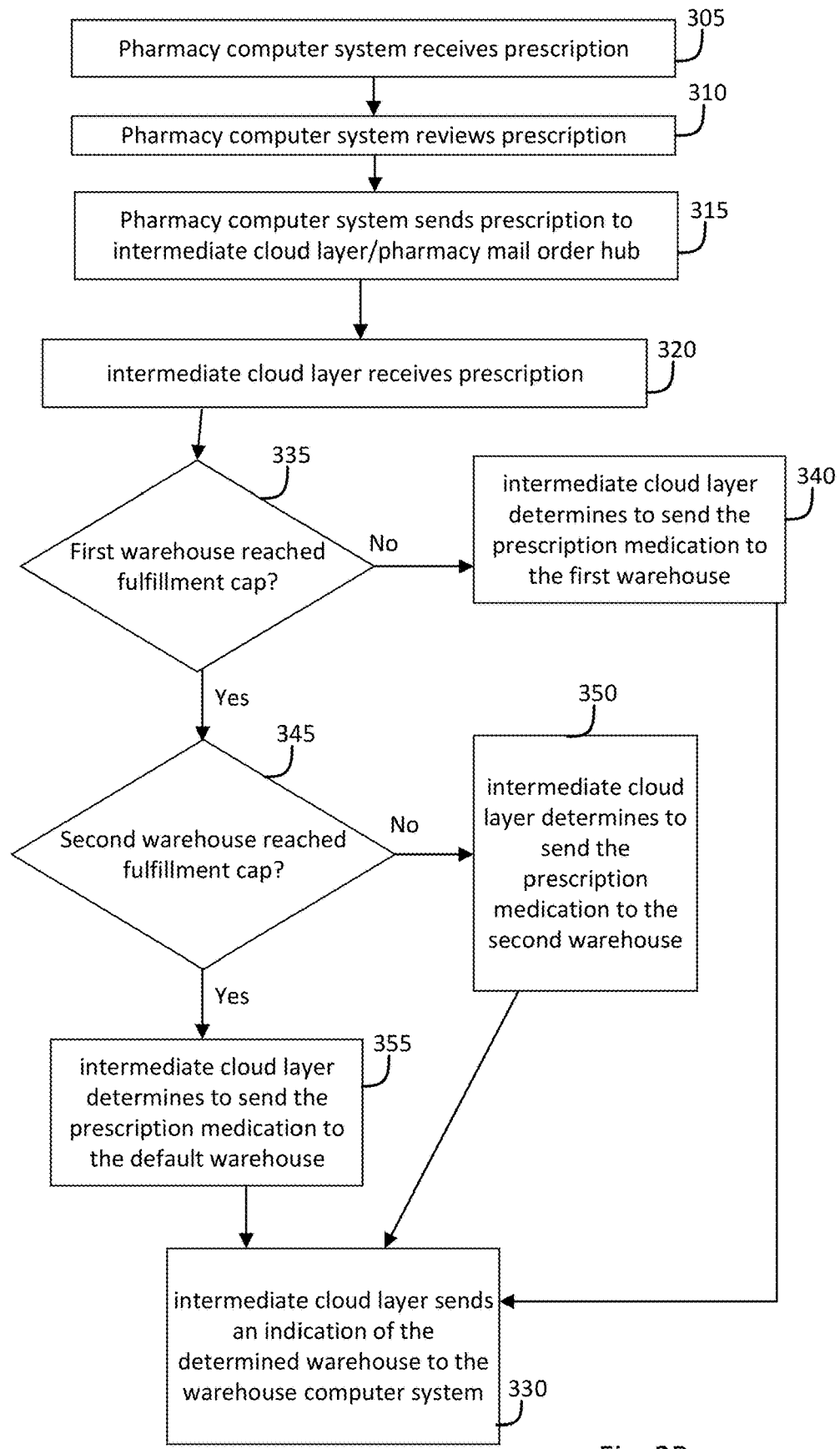
FIG. 3B shows a flowchart of an example process for facilitating delivery of prescription medication regarding fulfillment caps.

FIG. 3B shows a flowchart of an example implementation of facilitating delivery of prescription medication regarding fulfillment caps. With reference thereto, steps 305, 310, 315, 320, and 330 are preformed analogously to the example of FIG. 3A. At step 335, the intermediate cloud layer 171 determines if a first warehouse (e.g., an intermediate warehouse 155 or a central warehouse 160) has reached a fulfillment cap (e.g., a total number of medications that may be shipped to a warehouse in any one day, such as 500, 1,000, or 2,000 medications). The fulfillment caps may be specific to each warehouse, and based on factors such as storage space, docking space, equipment capacities, and so forth. If the fulfillment cap of the first warehouse has not been reached, the intermediate cloud layer 171 determines to send the prescription medication to the first warehouse at step 340. If the fulfillment cap of the first warehouse has been reached, the intermediate cloud layer 171 determines if a fulfillment cap of a second warehouse (e.g., an intermediate warehouse 155 or a central warehouse 160) has been reached at step 345. If the fulfillment cap of the second warehouse has not been reached, the intermediate cloud layer 171 determines to send the prescription medication to the second warehouse at step 350. If the fulfillment cap of the second warehouse has been reached, the intermediate cloud layer 171 determines to send the prescription medication to the default warehouse at step 355.

Figure 3C:
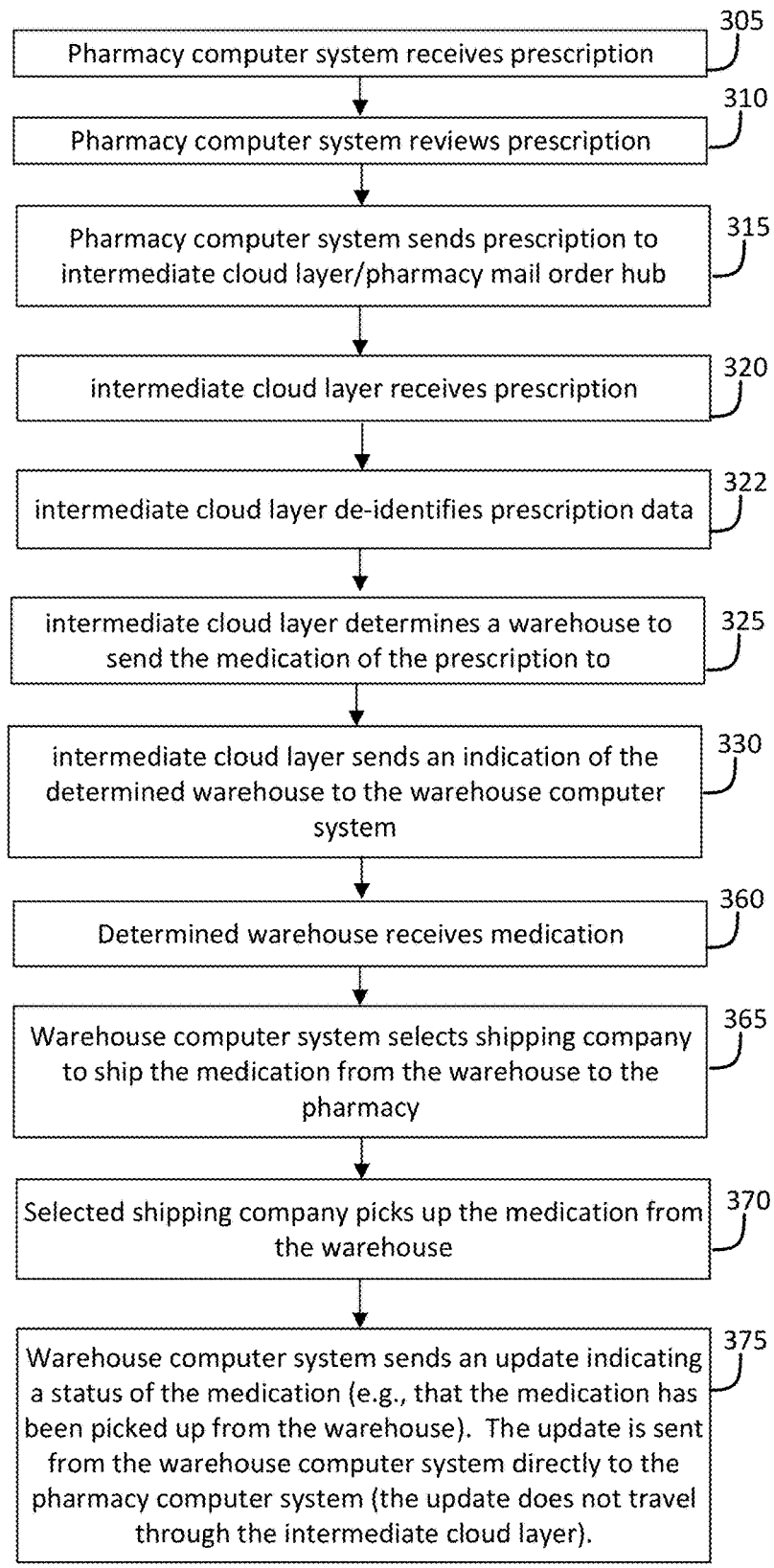
FIG. 3C shows a flowchart of an example process for facilitating delivery of prescription medication.

FIG. 3C shows a flowchart of another example implementation of facilitating delivery of prescription medication. With reference thereto, steps 305, 310, 315, 320, 325, and 330 are preformed analogously to the example of FIG. 3A. In the illustrated example of FIG. 3C, the intermediate cloud layer 171 further de-identifies the prescription data at step 322. Advantageously, this better preserves patient privacy because the warehouse computer system 181 never receives the patient identity data. Moreover, this further preserves patient privacy, while allowing the pharmacy computer system 101 to retain the patient identity data for health insurance purposes, or for purposes of retaining a patient's personal preferences (e.g., which pharmacy to fill a prescription at, and so forth).

At step 360, the determined warehouse receives the medication. At step 365, the warehouse computer system 181 selects a shipping company 165 to ship the medication from the warehouse to the pharmacy 166, or the combined pharmacy and retail store 167. At step 370, the selected shipping company 165 picks up the medication from the warehouse. At step 375, the warehouse computer system sends an update indicating a status of the medication (e.g., that the medication has been picked up from the warehouse). The update is sent from the warehouse computer system 181 directly to the pharmacy computer system 101 (the update does not travel through the intermediate cloud layer 171). Sending updates in this manner has the technical advantage of reducing the amount of data that needs to be processed (e.g., at the intermediate cloud layer 171), and further allows the updates to reach the pharmacy computer system 101 faster.

Further illustrated in FIG. 2 is enterprise data warehouse (EDW) 235 and accounting 240. In some embodiments, the EDW 235 is used for data analysis, and reporting data (e.g., to the pharmacy computer system 101). In some implementations, the EDW receives routing details (e.g., destination information of the medication) from the intermediate cloud layer. In some embodiments, the reporting feed process 230 prepares a daily extract file to be sent to the EDW 235, which advantageously reduces the amount of data that needs to be sent. Further, in some embodiments, the EDW 235 receives data from the pharmacy computer system 101; this allows the EDW 235 analyze and combine the data from the pharmacy computer system 101 and the intermediate cloud layer 171 before sending the combined data to accounting 240. Still further, in some embodiments, the EDW 235 is not in communication with the warehouse computer system 181, which advantageously improves privacy and security of patient data.

Furthermore, order clearance 225 may process files, such as ODC files, and use the processed files to update the database 175. In some embodiments, the processed files may then also be sent to the pharmacy computer system 101.

Additionally, voltage encryption/key vault 222 may be used for voltage field level encryption. In this regard, in some implementations, voltage may be used to encrypt key data attributes, such as identity data, medication data, prescription data, and so forth.

With further reference to FIG. 2, it should be understood that, in some implementations, the pharmacy computer engine 210 may comprise, wholly or partially, the server(s) 102, the CPU 104, and the memory 106; the routing engine 220 may comprise, wholly or partially, the server(s) 172, the CPU 174, and the memory 176; and the warehouse computer system engine 245 may comprise, wholly or partially, the server(s) 182, the CPU 184, and the memory 186.

Figure 4:
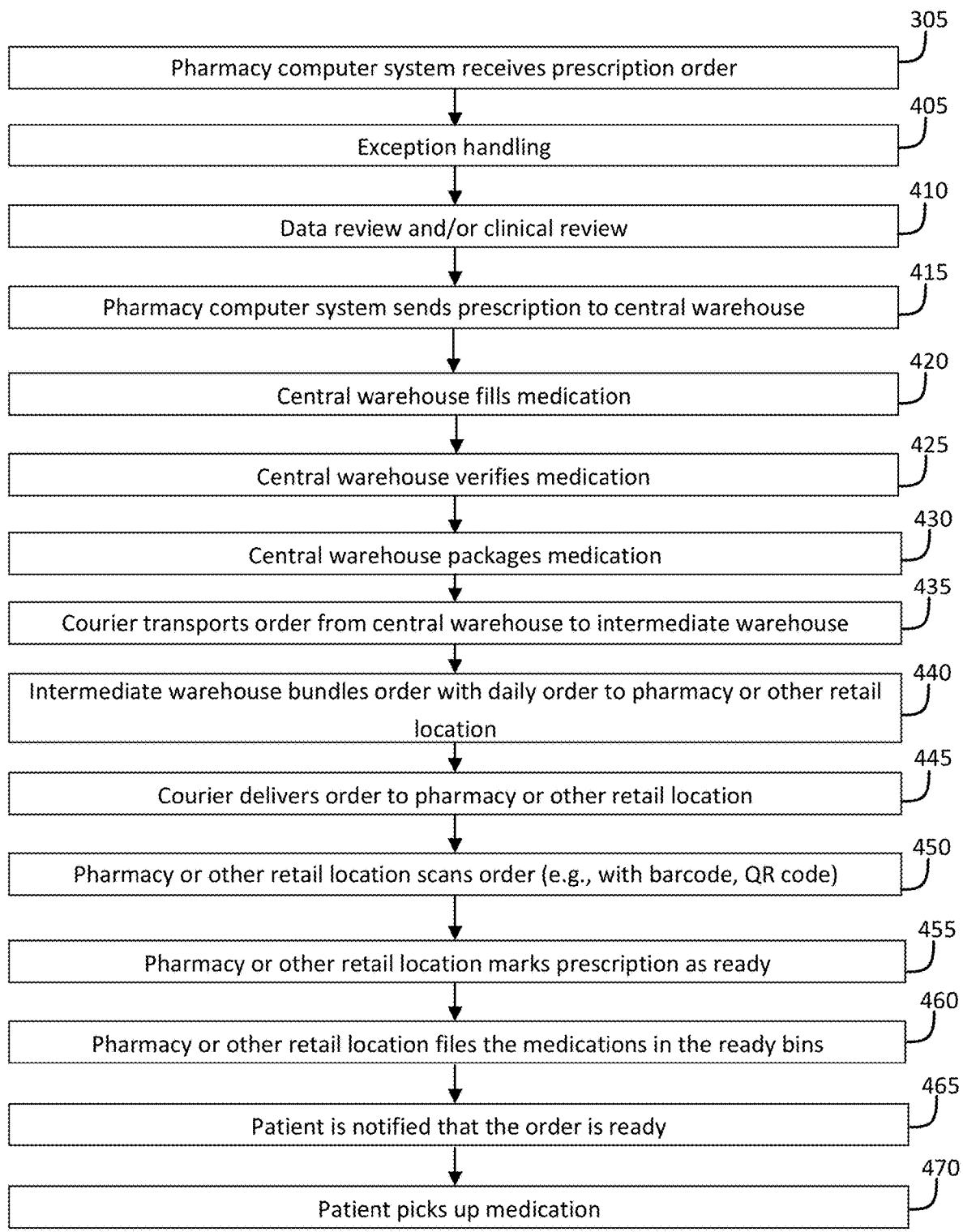
FIG. 4 shows a flowchart of an example process for facilitating delivery of prescription medication, including delivery from a central warehouse to an intermediate warehouse to a pharmacy.

FIG. 4 shows a flowchart of an example implementation of facilitating delivery of prescription medication, including delivery from a central warehouse 160 to an intermediate warehouse 155, and then to a pharmacy 166. With reference thereto, at step 305, the pharmacy computer system 101 receives a prescription (e.g., from a mobile device 111m or 113m). At step 405, the pharmacy computer system 101 performs exception handling. For example, the pharmacy computer system 101 may determine how to handle an incomplete prescription (e.g., prescription is missing dosage amount).

At step 410, the pharmacy computer system 101 performs a data review, a clinical review, and/or any other type of review. For example, the review may include determining if a conflict exists between a medication of the prescription and another medication of a patient of the prescription. In another example, the review may include determining an out of pocket payment for a patient of the prescription.

At step 415, the pharmacy computer system 101 sends the prescription to a central warehouse 160. At step 420, the central warehouse 160 fills the prescription. At step 425, the central warehouse 160 verifies the medication. At step 430, the central warehouse 160 packages the medication. At step 435, a courier transports the order from the central warehouse 160 to an intermediate warehouse 155. At step 440, the intermediate warehouse 155 bundles the order with a daily order to a pharmacy 166 or combined retail store and pharmacy 167. At step 445, the courier delivers the order. At step 450, the pharmacy 166 or combined retail store and pharmacy 167 scans the order (e.g., with a barcode or quick response (QR) code) to log that the order has arrived. At step 455, the pharmacy 166 or combined retail store and pharmacy 167 marks the prescription as ready. At step 460, the medication is filed in the ready bins. At step 465, the patient is notified that the order is ready. At step 470, the patient picks up the medication.

Figure 5A:
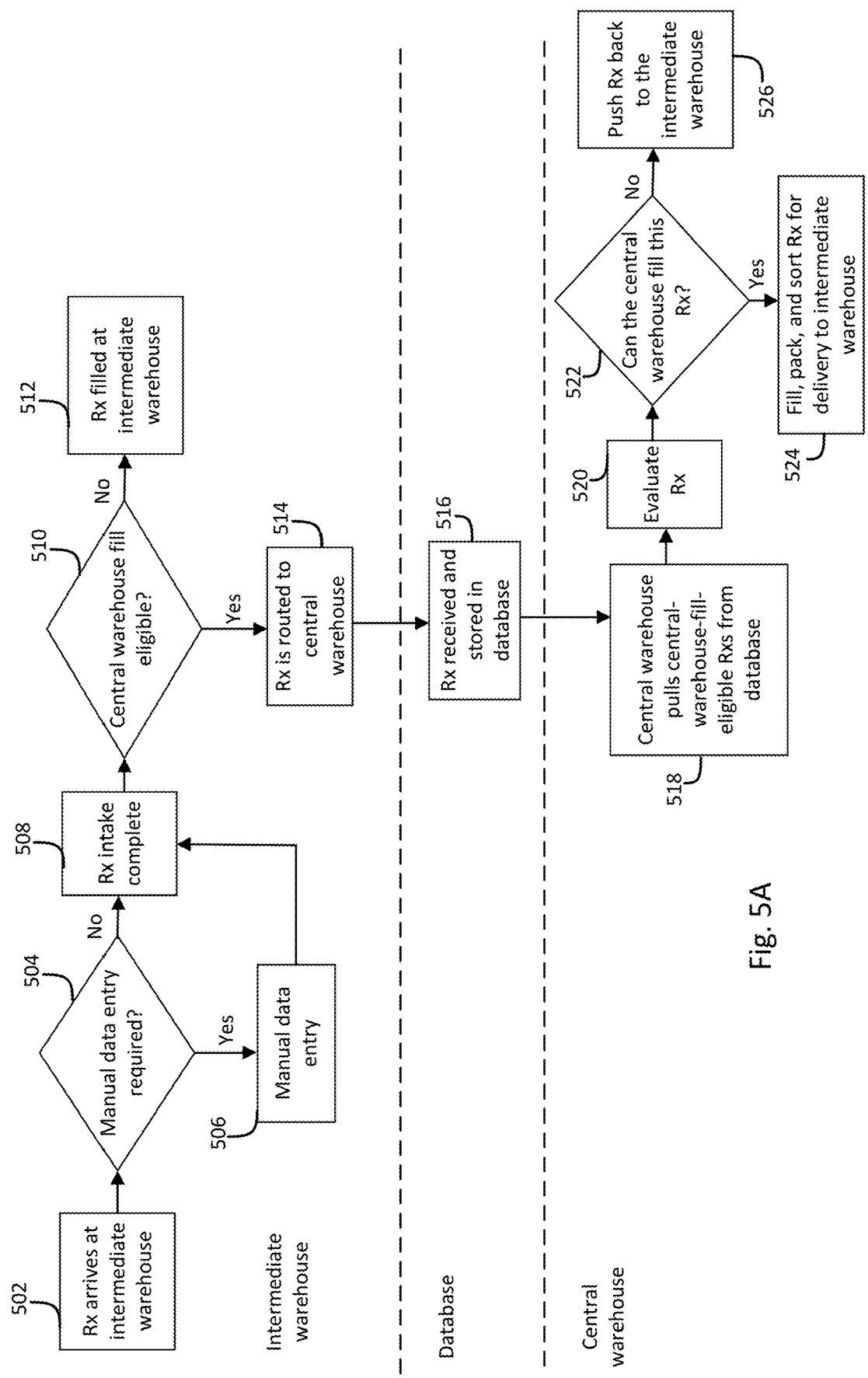
FIGS. 5A and 5B show a flowchart illustrating an example interaction between an intermediate warehouse and a central warehouse. In this regard.
Figure 5B:
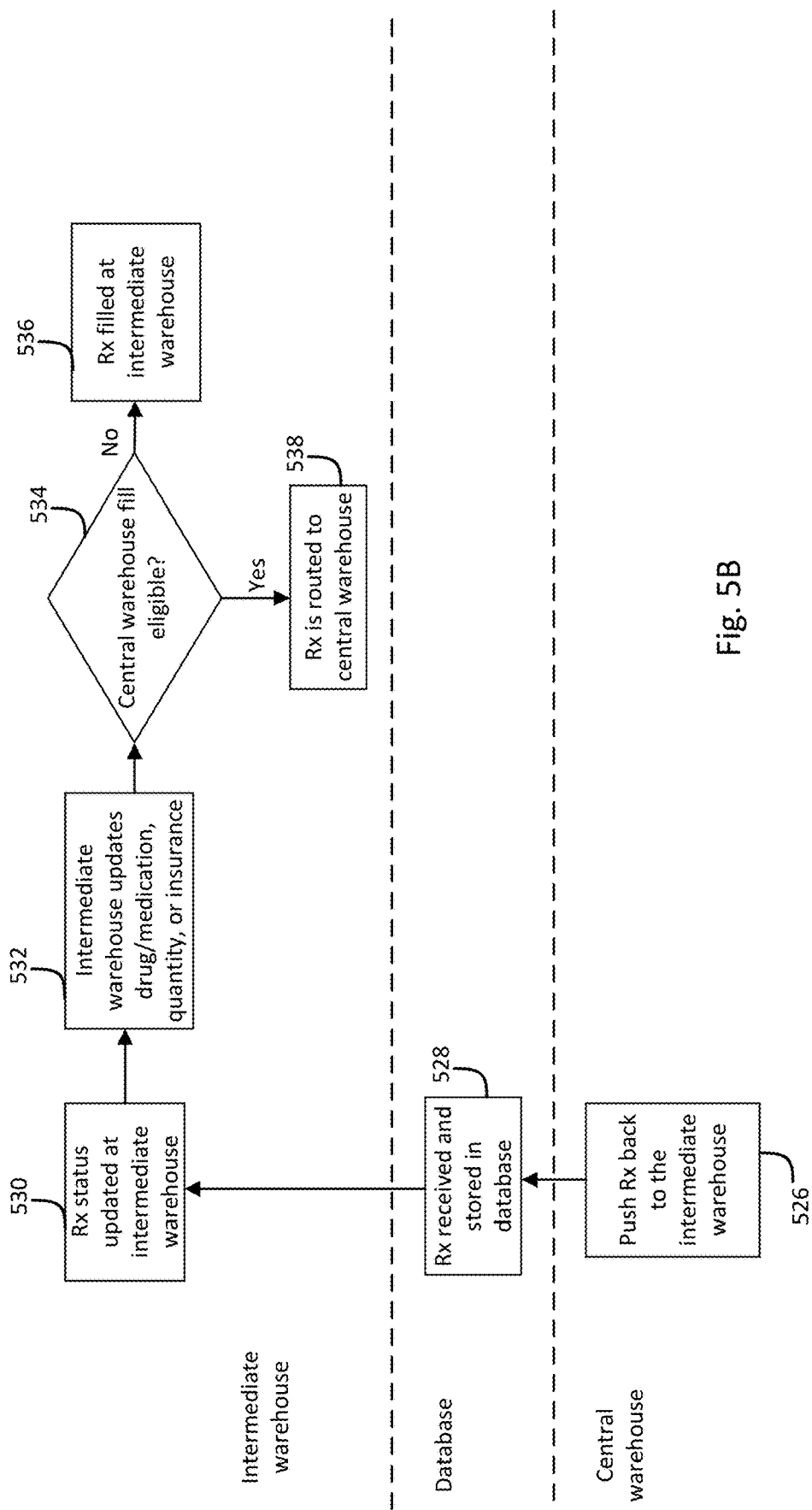

FIGS. 5A and 5B show a flowchart illustrating an example interaction between an intermediate warehouse and a central warehouse. In this regard, FIG. 5B is a continuation of the flowchart in FIG. 5A. With reference thereto, in some implementations, the depicted intermediate warehouse comprises a computer system of an intermediate warehouse; the depicted central warehouse comprises a computer system of a central warehouse; and the depicted database comprises an electronic database, such as database 185. In some embodiments, the illustrated intermediate warehouse (e.g., intermediate warehouse computer system) and the illustrated central warehouse (e.g., central warehouse computer system) are both part of the warehouse computer system 181. Generally, the central warehouses have larger storage capacity to store a larger amount of medications than the intermediate warehouses. However, the intermediate warehouses are generally located in closer geographic proximity to the pharmacies. Further, in some embodiments, the intermediate warehouses are preferred over the central warehouses to store certain medications or goods that are high cost and slow moving; for example, if the cost of a good or medication is above a cost threshold, and the average length of time that the good or medication takes to sell is also above a time threshold, the goods or medication would meet this criteria.

At step 502, the prescription (Rx) arrives at the intermediate warehouse. At step 504, it is determined if manual data entry is required. Examples of reasons that manual data entry may be required are: a prescription is missing information; a computer system is unable to decipher information from a scanned image; and the intermediate warehouse determines that there may be an error in the prescription such as because a conflict exists between the prescribed medication and an existing medication of the patient. If manual data entry is required, at step 506, data is reviewed and entered manually; at this step, in some embodiments, an exception flag is also set.

At step 508, the Rx intake becomes complete (either because no manual data entry was required, or because the data was entered manually). At step 510, it is determined if the Rx is eligible for central warehouse fill. In some embodiments, this is done by comparing the medication of the Rx to a list of medications that are eligible. If the Rx is not eligible to be filled by a central warehouse, at step 512, instructions are sent for the Rx to be filled at the intermediate warehouse.

If the medication is eligible for fill by a central warehouse, at step 514, the Rx is routed to the central warehouse. Further, at step 514, the exception flag may be removed and/or a status of the Rx is updated to indicate that the Rx is being routed to the central warehouse. In some implementations, the routing is done via a database. In such implementations, at step 516, the Rx is received and stored in the database. Such storing allows the central warehouse to pull the prescriptions that are eligible for central warehouse fill in batches, thus advantageously increasing efficiency. As illustrated, the central warehouse pulls the prescription(s) at step 518.

At step 520, the Rx is evaluated. At step 522, it is determined if the central warehouse can fill the Rx. For example, it is determined if the central warehouse has the medication in stock. Additionally, at step 522, the central warehouse may mark the Rx with an exception including a reason that the Rx is being pushed back. If the central warehouse can fill the Rx, the medication of the Rx is filled, packed, and sorted for delivery to the intermediate warehouse at step 524. If the central warehouse cannot fill the Rx, the Rx is pushed back to the intermediate warehouse at step 526. At step 528, the Rx is received and stored in the database. At step 530, the Rx status is updated at the intermediate warehouse. For example, the intermediate warehouse may read the exception with the reason that the Rx was pushed back, and update the Rx status to reviewed. At step 532, the intermediate warehouse updates a medication, quantity, and/or insurance of the Rx. At step 534, it is determined if the updated Rx is central warehouse fill eligible. If not, the Rx is filled at the intermediate warehouse at step 536. If so, the updated Rx is routed to the central warehouse at step 538.

ADDITIONAL EXEMPLARY EMBODIMENTS

Aspect 1. In one aspect, there is a computer system for facilitating delivery of prescription medication, the computer system comprising:

a pharmacy computer system comprising one or more processors configured to: (i) receive a prescription, (ii) review the prescription, and (iii) send the prescription to an intermediate cloud layer;

the intermediate cloud layer comprising one or more processors configured to:

receive the reviewed prescription from the pharmacy computer system;

determine, based on at least one criteria, a warehouse of a plurality of warehouses to send medication of the prescription to, wherein the at least one criteria comprises at least one of: (i) a health insurance plan; (ii) whether the medication comprises a controlled substance; (iii) whether the medication must be refrigerated during shipping; (iv) a warehouse shipping address; or (v) a fulfillment cap of a warehouse; and send an indication of the determined warehouse of the plurality of warehouses to a warehouse computer system.

Aspect 2. The computer system of aspect 1, wherein:

the at least one criteria comprises the fulfillment cap of the warehouse;

the plurality of warehouses comprises a first warehouse, a second warehouse, and a default warehouse;

each of the first and second warehouses has a fulfillment cap; and the one or more processors of the intermediate cloud layer are further configured to determine the warehouse to send the medication to by:

determining if the fulfillment cap of the first warehouse has been met;

if the fulfillment cap of the first warehouse has been met, determine if the fulfillment cap of the second warehouse has been met; and if the fulfillment cap of the second warehouse has been met, determine that the warehouse to send the medication to is the default warehouse.

Aspect 3. The computer system of aspect 1, wherein the one or more processors of the pharmacy computer system are configured to review the prescription by determining if a conflict exists between a medication of the prescription and another medication of a patient of the prescription.

Aspect 4. The computer system of aspect 1, wherein the one or more processors of the pharmacy computer system are configured to review the prescription by determining an out of pocket payment for a patient of the prescription.

Aspect 5. The computer system of aspect 1, further comprising the warehouse computer system, and wherein the warehouse computer system comprises one or more processors configured to select a shipping company to bring the medication from the determined warehouse to a pharmacy.

Aspect 6. The computer system of aspect 1, further comprising the warehouse computer system, and wherein the warehouse computer system comprises one or more processors configured to:

send updates directly to the pharmacy computer system, wherein: (i) the updates are not sent from the warehouse computer system to the intermediate cloud layer, and (ii) the updates comprise status information of the medication.

Aspect 7. The computer system of aspect 1, further comprising an enterprise data warehouse (EDW) comprising one or more processors configured to receive routing details from the intermediate cloud layer;

wherein the one more processors of the EDW are further configured to be in communication with the intermediate cloud layer; and wherein the one or more processors of the EDW are not configured to be in communication with one or more processors of the warehouse computer system.

Aspect 8. The computer system of aspect 1, wherein the one or more processors of the pharmacy computer system are configured to:

send, to the intermediate cloud layer, the prescription comprised in a first file, the first file having an order received (ODR) file format; and receive files from the intermediate cloud layer in an order completed (ODC) file format.

Aspect 9. The computer system of aspect 1, wherein:

the prescription sent from the pharmacy computer system to the intermediate cloud layer includes prescription data including identity data of a patient; and the one or more processors of the intermediate cloud layer are further configured to: (i) de-identify the prescription data, and (ii) send the de-identified prescription data to the warehouse computer system along with the determined warehouse of the plurality of warehouses.

Aspect 10. The computer system of aspect 1, wherein the at least one criteria comprises at least three of: (i) a health insurance plan; (ii) whether the medication comprises a controlled substance; (iii) whether the medication must be refrigerated during shipping; (iv) a warehouse shipping address; and (v) a fulfillment cap of a warehouse.

Aspect 11. The computer system of aspect 1, wherein the at least one criteria comprises all of: (i) a health insurance plan; (ii) whether the medication comprises a controlled substance; (iii) whether the medication must be refrigerated during shipping; (iv) a warehouse shipping address; and (v) a fulfillment cap of a warehouse.

Aspect 12. The computer system of aspect 1, wherein:

the determination made by the one or more processors of the intermediate cloud layer is a first determination and the determined warehouse is a first warehouse; and the one or more processors of the intermediate cloud layer are further configured to:

receive a second reviewed prescription from the pharmacy computer system; and determine a second warehouse of the plurality of warehouses to send the second medication of the second reviewed prescription to by reconfiguring the at least one criteria such that the at least one criteria used to determine the second warehouse is different than the at least one criteria used to determine the first warehouse.

Aspect 13. A computer-implemented method for facilitating delivery of prescription medication, the method comprising:

with one or more processors of a pharmacy computer system: (i) receiving a prescription, (ii) reviewing the prescription, and (iii) sending the prescription to an intermediate cloud layer comprising one or more processors;

with the one or more processors of the intermediate cloud layer:

receiving the reviewed prescription from the pharmacy computer system;

determining, based on at least one criteria, a warehouse of a plurality of warehouses to send medication of the prescription to, wherein the at least one criteria comprises at least one of: (i) a health insurance plan; (ii) whether the medication comprises a controlled substance; (iii) whether the medication must be refrigerated during shipping; (iv) a warehouse shipping address; or (v) a fulfillment cap of a warehouse; and sending an indication of the determined warehouse of the plurality of warehouses to a warehouse computer system.

Aspect 14. The computer-implemented method of aspect 13, further comprising:

reconfiguring the at least one criteria;

receiving a second reviewed prescription; and determining a second warehouse of the plurality of warehouses to send medication of the second reviewed prescription to based on the reconfigured at least one criteria.

Aspect 15. The computer-implemented method of aspect 13, wherein the reviewing of the prescription comprises determining if a conflict exists between a medication of the prescription and another medication of a patient of the prescription.

Aspect 16. The computer-implemented method of aspect 13, wherein the reviewing of the prescription comprises determining an out of pocket payment for a patient of the prescription.

Aspect 17. A computer system for facilitating delivery of prescription medication, the computer system comprising:

an intermediate warehouse computer system of an intermediate warehouse, the intermediate warehouse computer system comprising one or more processors configured to:

receive a prescription;

determine if the prescription is eligible to be filled by a central warehouse system;

if the prescription is not eligible to be filled by the central warehouse system, send instructions to fill the prescription at the intermediate warehouse; and if the prescription is eligible to be filled by the central warehouse system, route the prescription to a central warehouse; and a central warehouse computer system comprising one or more processors configured to:

pull the prescription from a database;

determine if the central warehouse can fill the prescription;

if the central warehouse can fill the prescription, send instructions to deliver medication of the prescription from the central warehouse to the intermediate warehouse; and if the central warehouse cannot fill the prescription, push the prescription back to the intermediate warehouse.

Aspect 18. The computer system of aspect 17, wherein the central warehouse has a larger capacity for medication storage than the intermediate warehouse.

Aspect 19. The computer system of aspect 17, further comprising:

the database, wherein the database is configured to receive the prescription routed from the intermediate warehouse computer system, and store the received prescription;

wherein the one or more processors of the central warehouse computer system are configured to pull the prescription from the database as part of a batch of prescriptions eligible for fill by the central warehouse.

Aspect 20. The computer system of aspect 17, wherein the one or more processors of the intermediate warehouse computer system are further configured to:

receive the prescription pushed back from the central warehouse computer system;

update a medication, quantity, or insurance of the prescription;

determine if the updated prescription is eligible to be filled by the central warehouse system;

if the updated prescription is not eligible to be filled by the central warehouse system, send instructions to fill the prescription at the intermediate warehouse; and if the updated prescription is eligible to be filled by the central warehouse system, route the updated prescription to a central warehouse.

OTHER MATTERS

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. A computer system for facilitating delivery of prescription medication, the computer system comprising:
  a pharmacy computer system comprising one or more processors configured to: (i) receive a prescription, (ii) review the prescription, and (iii) send the prescription to an intermediate cloud layer;
  the intermediate cloud layer comprising one or more processors configured to:
    receive the reviewed prescription from the pharmacy computer system;
    determine, based on at least one criteria, a warehouse of a plurality of warehouses to send medication of the prescription to, wherein the at least one criteria comprises at least one of: (i) a health insurance plan; (ii) whether the medication comprises a controlled substance; (iii) whether the medication must be refrigerated during shipping; (iv) a warehouse shipping address; or (v) a fulfillment cap of a warehouse; and
    send an indication of the determined warehouse of the plurality of warehouses to a warehouse computer system.

2. The computer system of claim 1, wherein:
  the at least one criteria comprises the fulfillment cap of the warehouse;
  the plurality of warehouses comprises a first warehouse, a second warehouse, and a default warehouse;
  each of the first and second warehouses has a fulfillment cap; and
  the one or more processors of the intermediate cloud layer are further configured to determine the warehouse to send the medication to by:
    determining if the fulfillment cap of the first warehouse has been met;
    if the fulfillment cap of the first warehouse has been met, determine if the fulfillment cap of the second warehouse has been met; and
    if the fulfillment cap of the second warehouse has been met, determine that the warehouse to send the medication to is the default warehouse.

3. The computer system of claim 1, wherein the one or more processors of the pharmacy computer system are configured to review the prescription by determining if a conflict exists between a medication of the prescription and another medication of a patient of the prescription.

4. The computer system of claim 1, wherein the one or more processors of the pharmacy computer system are configured to review the prescription by determining an out of pocket payment for a patient of the prescription.

5. The computer system of claim 1, further comprising the warehouse computer system, and wherein the warehouse computer system comprises one or more processors configured to select a shipping company to bring the medication from the determined warehouse to a pharmacy.

6. The computer system of claim 1, further comprising the warehouse computer system, and wherein the warehouse computer system comprises one or more processors configured to:
  send updates directly to the pharmacy computer system, wherein: (i) the updates are not sent from the warehouse computer system to the intermediate cloud layer, and (ii) the updates comprise status information of the medication.

7. The computer system of claim 1, further comprising an enterprise data warehouse (EDW) comprising one or more processors configured to receive routing details from the intermediate cloud layer;
  wherein the one more processors of the EDW are further configured to be in communication with the intermediate cloud layer; and
  wherein the one or more processors of the EDW are not configured to be in communication with one or more processors of the warehouse computer system.

8. The computer system of claim 1, wherein the one or more processors of the pharmacy computer system are configured to:
  send, to the intermediate cloud layer, the prescription comprised in a first file, the first file having an order received (ODR) file format; and
  receive files from the intermediate cloud layer in an order completed (ODC) file format.

9. The computer system of claim 1, wherein:
  the prescription sent from the pharmacy computer system to the intermediate cloud layer includes prescription data including identity data of a patient; and
  the one or more processors of the intermediate cloud layer are further configured to: (i) de-identify the prescription data, and (ii) send the de-identified prescription data to the warehouse computer system along with the determined warehouse of the plurality of warehouses.

10. The computer system of claim 1, wherein the at least one criteria comprises at least three of: (i) a health insurance plan; (ii) whether the medication comprises a controlled substance; (iii) whether the medication must be refrigerated during shipping; (iv) a warehouse shipping address; and (v) a fulfillment cap of a warehouse.

11. The computer system of claim 1, wherein the at least one criteria comprises all of: (i) a health insurance plan; (ii) whether the medication comprises a controlled substance; (iii) whether the medication must be refrigerated during shipping; (iv) a warehouse shipping address; and (v) a fulfillment cap of a warehouse.

12. The computer system of claim 1, wherein:
the determination made by the one or more processors of the intermediate cloud layer is a first determination and the determined warehouse is a first warehouse; and
the one or more processors of the intermediate cloud layer are further configured to:
receive a second reviewed prescription from the pharmacy computer system; and
determine a second warehouse of the plurality of warehouses to send the second medication of the second reviewed prescription to by reconfiguring the at least one criteria such that the at least one criteria used to determine the second warehouse is different than the at least one criteria used to determine the first warehouse.

13. A computer-implemented method for facilitating delivery of prescription medication, the method comprising:
with one or more processors of a pharmacy computer system: (i) receiving a prescription, (ii) reviewing the prescription, and (iii) sending the prescription to an intermediate cloud layer comprising one or more processors;
with the one or more processors of the intermediate cloud layer:
receiving the reviewed prescription from the pharmacy computer system;
determining, based on at least one criteria, a warehouse of a plurality of warehouses to send medication of the prescription to, wherein the at least one criteria comprises at least one of: (i) a health insurance plan; (ii) whether the medication comprises a controlled substance; (iii) whether the medication must be refrigerated during shipping; (iv) a warehouse shipping address; or (v) a fulfillment cap of a warehouse; and
sending an indication of the determined warehouse of the plurality of warehouses to a warehouse computer system.

14. The computer-implemented method of claim 13, further comprising:
reconfiguring the at least one criteria;
receiving a second reviewed prescription; and
determining a second warehouse of the plurality of warehouses to send medication of the second reviewed prescription to based on the reconfigured at least one criteria.

15. The computer-implemented method of claim 13, wherein the reviewing of the prescription comprises determining if a conflict exists between a medication of the prescription and another medication of a patient of the prescription.

16. The computer-implemented method of claim 13, wherein the reviewing of the prescription comprises determining an out of pocket payment for a patient of the prescription.

* * * * *